United States Patent
Dilger et al.

(10) Patent No.: US 6,654,470 B1
(45) Date of Patent: Nov. 25, 2003

(54) FREQUENCY WARPING FOR IMPROVING RESONATOR SIGNAL-TO-NOISE RATIO

(75) Inventors: John P. Dilger, Marshalltown, IA (US); Guojun Liu, Ames, IA (US)

(73) Assignee: Fisher-Rosemount Systems, Inc., Austin, TX (US)

( * ) Notice: Subject to any disclaimer, the term of this patent is extended or adjusted under 35 U.S.C. 154(b) by 0 days.

(21) Appl. No.: 09/352,730

(22) Filed: Jul. 13, 1999

(51) Int. Cl.[7] .......................... H04B 15/00; G01N 29/02
(52) U.S. Cl. ..................... 381/94.1; 73/24.06; 331/94.1
(58) Field of Search .................. 381/94.1, 61, 124; 73/24.01, 24.06, 24.05; 331/94.1, 3; 333/189

(56) References Cited

U.S. PATENT DOCUMENTS

| | | | |
|---|---|---|---|
| 3,260,104 A | * 7/1966 | King, Jr. | ..................... 73/24.06 |
| 3,921,093 A | * 11/1975 | Lewis | ........................ 331/94.1 |
| 4,361,026 A | 11/1982 | Muller et al. | .................. 73/223 |
| 4,905,701 A | 3/1990 | Cornelius | .............. 128/660.01 |
| 5,212,988 A | 5/1993 | White et al. | ................... 73/599 |
| 5,229,735 A | * 7/1993 | Quan | ..................... 331/116 R |
| 5,604,335 A | 2/1997 | Isahaya | ....................... 177/210 |
| 5,705,399 A | 1/1998 | Larue | ........................ 436/501 |
| 6,222,366 B1 | * 4/2001 | Dilger | ....................... 73/24.06 |
| 6,237,397 B1 | * 5/2001 | Shinar et al. | .............. 73/24.06 |

OTHER PUBLICATIONS

Leo G. Sands and Donald R. Mackenroth, *Encyclopedia of Electronic Circuits*, 1975, pp. 205–206, published by Parker Publishing Company, Inc.

* cited by examiner

*Primary Examiner*—Xu Mei
(74) *Attorney, Agent, or Firm*—Kinney & Lange, P.A.

(57) ABSTRACT

A sensor circuit for use in measuring concentrations of an analyte in a fluid is comprised of a BAW sensor, a voltage variable capacitor connected to the sensor, an input which supplies a bias warping dc voltage to the voltage variable capacitor, and a resonant oscillator circuit. The resonant oscillator circuit detects the fundamental frequency of the sensor and produces a resonant signal frequency. The bias warping dc voltage applied to the voltage variable capacitor warps the resonant frequency of the circuit away from inharmonic noise.

13 Claims, 2 Drawing Sheets

FREQUENCY WARPING FOR IMPROVING RESONATOR SIGNAL-TO-NOISE RATIO

CROSS-REFERENCE TO RELATED APPLICATION(S)

None.

BACKGROUND OF THE INVENTION

Bulk acoustic wave (BAW) chemical sensors are used to measure the concentration of constituents or analyte in fluids (gases and liquids). These acoustic wave devices are typically constructed of piezoelectric crystals coated on at least one side with a material that has an affinity for the analyte whose concentration is to be measured. The device is placed in the fluid stream containing the analyte to be measured, and the analyte is adsorbed or absorbed onto the coated surface. The amount of analyte adsorbed or absorbed by the acoustic wave device increases the mass of the device and alters the viscoelastic properties at the surface of the device, thereby damping the acoustic wave properties of the device. As a result, the frequency at which the acoustic wave device will resonant is altered.

When the acoustic wave device is incorporated into an electrical oscillator circuit, the change in resonant frequency of the device changes the operating frequency of the oscillator. The concentration of the analyte can be determined by measuring the change in operating frequency of the oscillator circuit over time.

These chemical sensors are designed to operate in specific ranges of environmental conditions, such as temperature (e.g.,–10° C. to 50° C.) and humidity (e.g., 0% to 90% relative humidity) and are capable of detecting small concentrations, and small changes of concentrations, of the targeted analyte. However, small changes in analyte concentrations can produce small changes in the resonant frequency of the crystal. Thus, for example, a small concentration of analyte being measured might alter the nominal resonant frequency of a 10 MHz crystal by about 200 Hz. Therefore, the detection circuit must be capable of detecting the resonant frequency of the crystal with high accuracy.

However, the viscoelastic properties of the device can be affected by thermal dynamic conditions to which the device is subjected. More particularly, temperature and humidity can "age" the characteristics of the crystal, causing permanent alteration of the viscoelastic properties of the crystal. This alteration of viscoelastic properties affects the dynamic characteristics of the device, and hence the velocity of resonance in the crystal forming the device. Alteration of the resonant properties of the crystal often creates inharmonic mode responses, which generate noise in the operating frequency of the oscillator circuit. Therefore, it is important to eliminate the effects of noise in the detection circuit.

BRIEF SUMMARY OF THE INVENTION

This invention utilizes time domain signal processing to reduce the inharmonic noise which distorts the fundamental frequency of a bulk acoustic wave sensor.

One form of the invention is a process for reducing the inharmonic noise which distorts the fundamental frequency of the sensor. A voltage variable capacitor is placed in series with the sensor to create a voltage-controlled oscillator. The voltage-controlled oscillator is placed in parallel with a resonant oscillator to form a circuit having a resonant frequency. A reverse bias direct current (dc) voltage is applied across the voltage variable capacitor to alter its capacitance thereby warping the resonant frequency away from inharmonic noise frequencies.

Another form of the invention is a sensor circuit for use in measuring the concentration of analytes in a fluid. The circuit includes a bulk acoustic wave sensor. A voltage variable capacitor is connected to the sensor. An input supplies a bias warping dc voltage to the capacitor. A resonant oscillator circuit detects the fundamental frequency of the sensor, and produces a resonant signal frequency. The bias dc voltage applied to the voltage variable capacitor warps the resonant frequency of the circuit away from the inharmonic noise frequencies.

In one form, the sensor and capacitor are connected in series to form a voltage-controlled oscillator which, in turn, is connected in parallel to the resonant oscillator.

DETAILED DESCRIPTION

Figure 1:
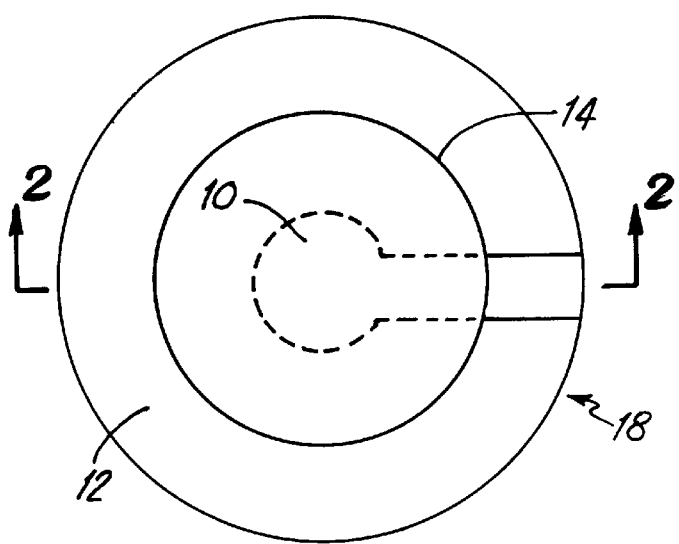
FIG. 1 is a top view of a bulk acoustic wave chemical sensor employed in the preferred embodiment of the present invention.
Figure 2:
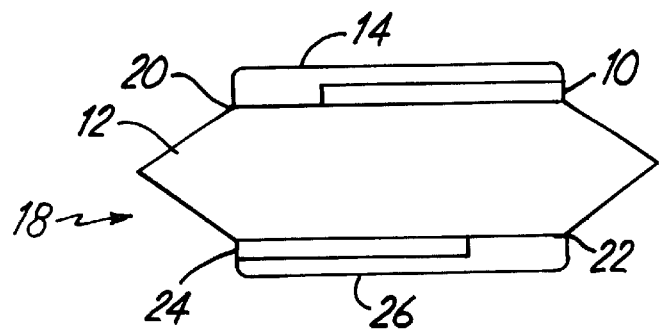
FIG. 2 is a section view of the sensor shown in FIG. 1 taken at line 2—2.

FIG. 1 is a top view, and FIG. 2 is a section view, of a bulk acoustic wave (BAW) sensor 18 employed in the presently preferred embodiment. Gold electrodes 10 and 24 are deposited to a thickness of about 300 Angstroms (Å) onto a 50 Å chromium seedlayer on opposite surfaces 20 and 22 of substrate 12. A 0.1 to 8 micron polymer film 14 is deposited onto electrode 10 and exposed portions of surface 20. Optionally, a second layer 26 of the same polymer material is deposited onto the bottom electrode 24 and exposed portion of surface 22. In either case, the polymer material has an affinity for the analyte to be measured. Sensor 18 is placed in a stream containing the analyte to be measured and the analyte is absorbed or adsorbed onto the coated surface. The thickness of substrate 12 together with electrodes 10 and 24 and films 14 and 26 define the resonant frequency of the device. As one or both polymer films absorb or adsorb analyte, the resonant frequency of the device changes. Electrodes 10 and 24 include terminals for connection of sensor 18 to respective circuit elements in FIG. 4.

Figure 3:
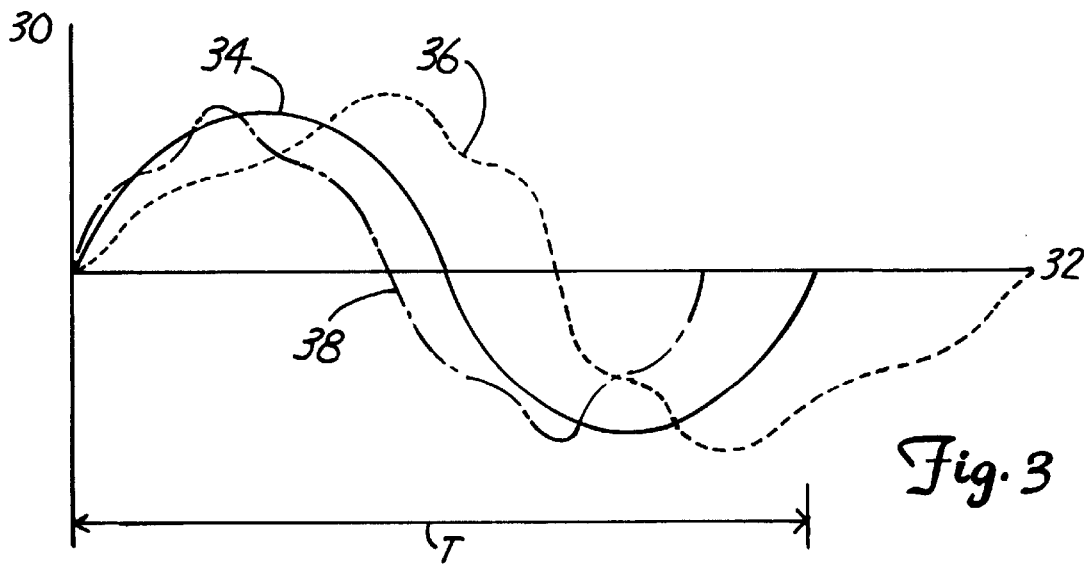
FIG. 3 is a frequency diagram showing the inharmonic modes which can distort the fundamental frequency of the sensor shown in FIGS. 1 and 2.

FIG. 3 is a frequency diagram showing potential effects of inharmonic distortion of the fundamental frequency of sensor 18. Signal amplitude is plotted on axis 30, and time is plotted on axis 32. T indicates the period of oscillation; the fundamental frequency is therefore 1/T. FIG. 3 shows signal distortion caused by inharmonic modes that pull away from the fundamental frequency of sensor 18. These inharmonic modes shift the fundamental frequency of the sensor by as much as 1 kilohertz (KHz) to 10 KHz, depending on various factors. For example, artifacts in sensor 18 can produce thickness shear modes. Stress and damping characteristics also change with time and become more noticeable, causing the distortion shown in FIG. 3. In addition, the viscoelastic properties and dynamic loss characteristics (i.e. the motional parameters) of sensor 18 can intensify the inharmonic mode distortion over varying thermodynamic conditions. Temperature and humidity "age" the crystal of sensor 18, causing permanent alteration of its viscoelastic properties.

In any case, alteration of the resonant properties of sensor 18 creates inharmonic modes, and generates noise in the operating frequency of the sensor. Waveform 34 shows the undisturbed fundamental frequency generated by sensor 18. Waveform 36 shows a distorted fundamental caused by an inharmonic mode that pulls down, or reduces, the fundamental frequency. Waveform 38 shows a distorted fundamental caused by an inharmonic mode that pulls up, or increases, the fundamental frequency.

Figure 4:
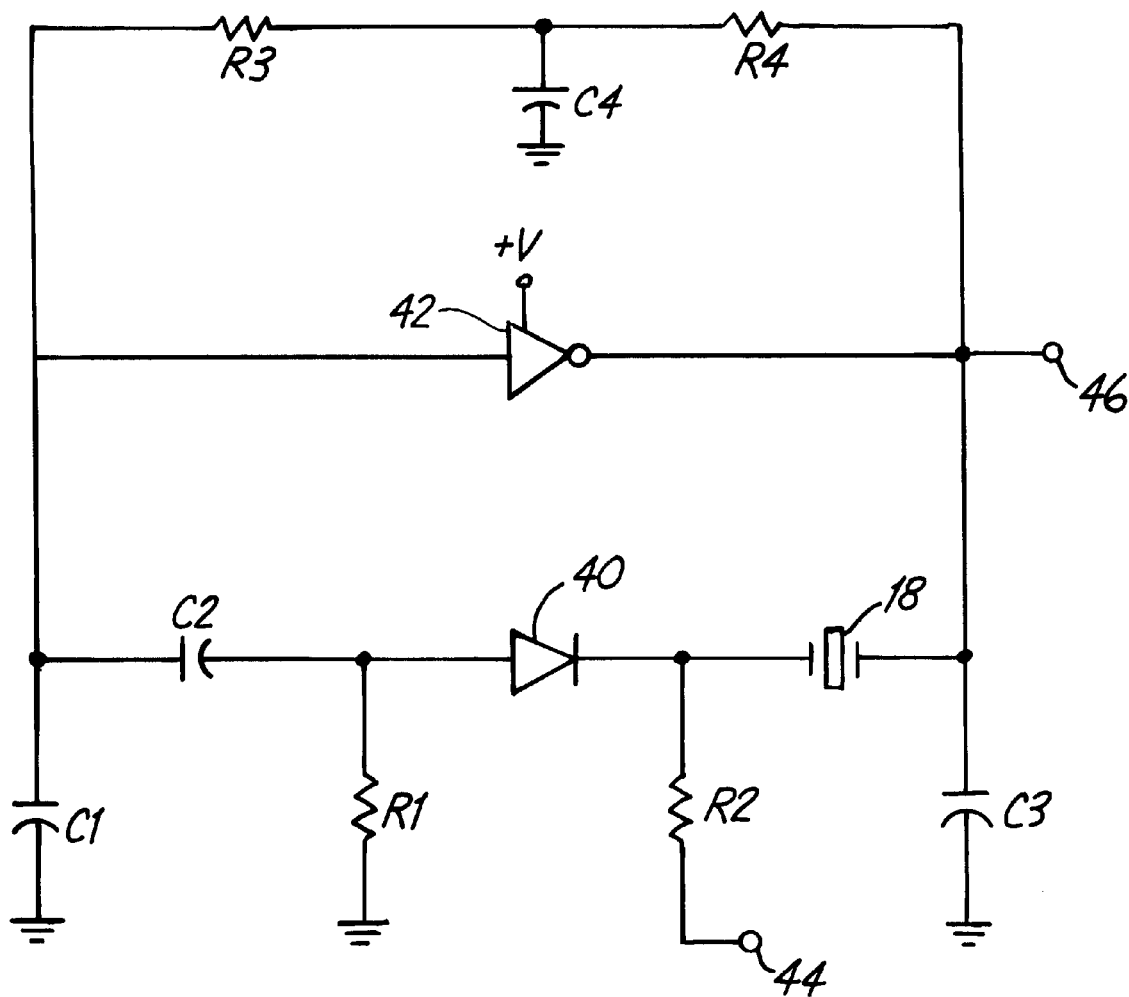
FIG. 4 is a circuit illustrating the implementation of the preferred embodiment of the present invention.

FIG. 4 is a circuit diagram of the preferred embodiment of the invention that warps a resonant frequency of the detection oscillator associated with the sensor. The circuit utilizes time domain signal processing, and is comprised of a voltage-controlled oscillator circuit in parallel with a resonant oscillator circuit.

The voltage-controlled oscillator circuit includes sensor 18, varactor 40, reference bias capacitor C2, summing resistors R1 and R2, phase shifting capacitors C1 and C3, and input 44. Sensor 18 has one of its terminals connected to phase shifting capacitor C3, which in turn is connected to ground. The second terminal of sensor 18 is connected through summing resistor R2 to input 44, and to the cathode of varactor 40. Varactor 40 is preferably a Zetex Hyper-Hyperabrupt variable capacitance diode, type ZC932. Varactor 40 functions as a voltage variable capacitor. Increasing the reverse bias voltage across varactor 40 reduces its capacitance.

The anode of varactor 40 is connected through second summing resistor R1 to ground, and to reference bias capacitor C2. Reference bias capacitor C2 is also connected through second phase shifting capacitor C1 to ground.

The resonant oscillator circuit is connected in parallel with the voltage controlled oscillator circuit. In the presently preferred embodiment, the resonant oscillator circuit includes inverter 42 which is also connected to supply +V, resistors R3 and R4, and tuning capacitor C4. Resistor R3 is connected to the input of inverter 42, and also through capacitor C4 to ground. Resistor R4 is also connected through capacitor C4 to ground, and also in the output of inverter 42. The input of inverter 42 is connected to the junction of capacitors C1 and C2; and the output of inverter 42 is inverted to the junction of sensor 18 and capacitor C3, and to output 46. Inverter 42 is a high gain linear amplifier. Voltage+V supplies the power to the resonant oscillator circuit.

Input voltage 44 provides a reverse bias dc voltage to the cathode of varactor 40. The value of the bias voltage is established by the summing resistors R1 and R2, as well as by capacitor C2. Capacitors C1 and C3 are phase shifting capacitors which enable start up of the circuit. The variable reactive load of varactor 40, in series with sensor 18, forces a change in the resonant frequency of sensor 18. The amount of the change is based on the values of resistors R1 and R2 and the bias dc voltage input at 44. Output 46 provides a signal with an adjusted resonant frequency, minus the inharmonic tones. Output 46 is connected to a high resolution counter, such as the one described in application Ser. No. 08/968,081, filed Nov. 12, 1997, for "High Frequency Measuring Circuit" by John P. Dilger and Nile K. Dielschneider, and assigned to the same assignee as the present application. The present invention significantly reduces the noise distortion that results in frequency shifting, or skipping, and it significantly enhances the resolution of 18.

Under normal conditions, the sensor 18, with a nominal frequency of 10 MHz, typically oscillates with a maximum error of approximately 10 Hertz (Hz). However, as noted previously, the inharmonic mode oscillations can cause frequency skipping, thereby pulling the fundamental frequency away from its 10 megahertz (MHz) value by as much as 1 to 10 KHz (representing a distortion of 0.01% to 0.1%). Sensor 18, however, must have a high resolution to measure small changes in analyte concentrations. For example, concentrations of analyte being measured may alter the initial 10 MHz frequency of sensor 18 by about 200 Hz (representing a change of 0.002%). Therefore, the frequency changes being measured as indications of change of analyte concentrations are within the changes of distortion caused by the inharmonic modes. Hence, the distortion must be effectively eliminated. With appropriate establishment of values of the circuit elements shown in FIG. 4, the frequency warping mechanism will pull the resonant frequency of the circuit back towards the 10 MHz fundamental value of the sensor. Thus, where distortion might alter the fundamental frequency of the sensor by 10 KHz (e.g. to 9.990 MHz), the warping circuit will pull the initial resonant frequency of the circuit back to 10.0 MHz through proper selection of resistors R1 and R2 and bias dc voltage value. Hence, deviation from the initial frequency is a true measure of analyte concentration, unaffected by noise.

The reverse bias dc voltage supplied by 44 is applied with voltage levels of 1, 2.5 and 4 volts. The amount of voltage applied by 44 is determined by the observed amount of noise distortion generated by sensor 18, and therefore by the amount of frequency warping needed. The selected reverse bias voltage is applied across 40 to provide a selected capacitance to varactor 40. For example, bias dc voltage levels of 1, 2.5 and 4 volts affects varactor 40 to provide capacitance of 17, 9 and 5 picofarad (pF), respectively, in a Zetex ZC932 diode. Typically, R1 and R2 have values of about 100 K ohms.

Although the present invention has been described with reference to preferred embodiments, workers skilled in the art will recognize that changes may be made in form and detail without departing from the spirit and scope of the invention.

What is claimed is:

1. A process for reducing effects of inharmonic noise which distorts a signal of a bulk acoustic wave sensor, the signal having a fundamental frequency, and the noise having one or more noise frequencies, the process comprising:

placing a voltage variable capacitor in series with the sensor to create a voltage-controlled oscillator;

placing the voltage-controlled oscillator in parallel with a resonant oscillator to form a circuit having a resonant frequency;

applying a reverse bias dc voltage across the voltage variable capacitor to alter its capacitance; and warping the resonant frequency away from inharmonic noise frequencies.

2. A sensor circuit for use in measuring concentrations of an analyte in a fluid comprising:

a bulk acoustic wave sensor;

a voltage variable capacitor connected to the sensor;

an input for supplying a bias warping dc voltage to the voltage variable capacitor; and a resonant oscillator circuit which detects a fundamental frequency of the sensor and produces a resonant signal frequency, whereby the bias warping dc voltage applied to the voltage variable capacitor warps the resonant frequency of the circuit away from inharmonic noise.

3. The circuit of claim 2, wherein the sensor comprises:

a crystal substrate having first and second opposite surfaces defining a predetermined thickness;

a first electrode on the first surface;

a second electrode on the second surface;

a first layer of material having an affinity to the predetermined analyte on at least a portion of the first electrode; and the first and second electrodes and the first layer having respective thicknesses so that the crystal substrate resonates at a predetermined fundamental frequency, the crystal substrate changing its fundamental frequency upon exposure of the first layer of the crystal to the analyte.

4. The circuit of claim 2, wherein the voltage variable capacitor is a variable capacitance diode having a cathode and an anode, and the input is connected to the cathode.

5. The circuit of claim 2, wherein the input is connected to the sensor and the voltage variable capacitor.

6. The circuit of claim. 2, wherein the voltage variable capacitor is connected in series to the sensor to form a voltage-controlled oscillator.

7. The circuit of claim 6, wherein the resonant oscillator circuit is in parallel with the voltage-controlled oscillator.

8. The circuit of claim 7, wherein the voltage-controlled oscillator further includes:

a phase shifting capacitor connected to a first side of the sensor; and a summing resistor connected between the input and a junction between the voltage variable capacitor and a second side of the sensor.

9. The circuit of claim 8, wherein the voltage-controlled oscillator further includes:

a reference bias capacitor connected in series with the voltage variable capacitor.

10. The circuit of claim 9, wherein the voltage-controlled oscillator further includes:

a second phase shifting capacitor connected to the reference bias capacitor.

11. The circuit of claim 10, wherein the voltage-controlled oscillator further includes:

a second summing resistor connected to a junction between the reference bias capacitor and the voltage variable capacitor.

12. The circuit of claim 7, wherein the resonant oscillator circuit comprises:

a logic inverter connected in parallel with the voltage-controlled oscillator, the inverter being connected to a power source;

first and second resistors connected in parallel with the inverter; and a turning capacitor connected between a reference and a junction between the first and second resistors.

13. The circuit of claim 12, wherein the logic inverter is as a high-gain linear amplifier, and has an input and an output.

* * * * *